United States Patent [19]
Hatfield

[11] Patent Number: 5,266,487
[45] Date of Patent: Nov. 30, 1993

[54] APPARATUS FOR THE TREATMENT OF LIGNOCELLULOSIC MATERIALS

[75] Inventor: G. Wesley Hatfield, Corona del Mar, Calif.

[73] Assignee: Knobbe, Martens, Olson & Bear, Newport Beach, Calif.

[21] Appl. No.: 957,592

[22] Filed: Oct. 6, 1992

Related U.S. Application Data

[63] Continuation of Ser. No. 724,431, Jun. 28, 1991, abandoned, which is a continuation of Ser. No. 245,711, Sep. 16, 1988, abandoned, which is a continuation-in-part of Ser. No. 47,658, May 8, 1987, Pat. No. 5,234,827, which is a continuation-in-part of Ser. No. 825,856, Feb. 4, 1986, Pat. No. 4,920,055.

[51] Int. Cl.$^5$ .......................... C12P 7/24; C12N 9/04; C12N 1/32
[52] U.S. Cl. .................... 435/288; 435/190; 435/311; 435/819; 422/187; 422/189; 422/206; 162/239; 162/246; 162/251; 162/261
[58] Field of Search ............... 435/277, 288, 311, 190, 435/819; 422/187, 189, 206; 162/78, 96, 97, 98, 99, 246, 239, 251, 261

[56] References Cited

U.S. PATENT DOCUMENTS

| | | | |
|---|---|---|---|
| 4,451,567 | 5/1984 | Ishibashi et al. | 435/170 |
| 4,649,113 | 3/1987 | Gould | 435/165 |
| 4,680,263 | 7/1987 | Yamada et al. | 435/162 |
| 4,920,055 | 4/1990 | Holberg et al. | 435/147 |

Primary Examiner—James C. Housel
Assistant Examiner—N. Bhat
Attorney, Agent, or Firm—Knobbe, Martens, Olson & Bear

[57] ABSTRACT

An apparatus is disclosed for treating lignocellulosic materials, comprising an enzymatic conversion zone adapted to enzymatically convert alcohol to aldehyde and hydrogen peroxide, a delignification zone, a device for transferring an effluent comprising aqueous hydrogen peroxide from the conversion zone to the delignification zone, a chopper for adding chopped lignocellulosic material to the delignification zone, a separator for separating solid delignified material in the delignification zone from a liquid, and a fermenter adapted to grow alcohol oxidase-producing yeast, and means for transferring alcohol oxidase from the fermenter into the conversion zone.

11 Claims, 1 Drawing Sheet

APPARATUS FOR THE TREATMENT OF LIGNOCELLULOSIC MATERIALS

This application is a continuation of application Ser. No. 07/724,431, filed Jun. 28, 1991, now abandoned which is a continuation of Ser. No. 07/245,711, filed Sep. 16, 1988, now abandoned. This is also a continuation in part of U.S. application Ser. No. 07/047,658, filed May 8, 1987, now U.S. Pat. No. 5,234,827 which is a continuation in part of U.S. application Ser. No. 06/825,856, filed Feb. 4, 1986, now U.S. Pat. No. 4,920,055.

BACKGROUND OF THE INVENTION

Lignocellulosic materials represent a major renewable energy and carbon source. Unfortunately, the chemical and physical structures of the vast majority of lignocellulosic materials hamper efficient utilization of this material for many purposes. This invention relates to a lignocellulose treatment process using low cost chemical feedstocks. The process economically converts lignocellulosics to a usable form.

The structure of lignocellulose fibers varies widely depending on the source. However, most lignocellulosic materials are complex structures comprising cellulose, hemicellulose and lignin as major constituents.

Cellulose itself is a variable polysaccharide, commonly a linear polymer of D-anhydroglucopyranose units connected with $\beta$-1-4-glucosidic bonds.

Hemicellulose exhibits wide variation in composition; however, hemicellulose commonly comprises polymers or heteropolymers of galactose, mannose, xylose, arabinose, and other sugars, together with uronic acids derived from those sugars. Hemicellulose generally exhibits a degree of polymerization of up to about 200 sugar moieties.

Lignin is a cross-linked three-dimensional polymer of aromatic alcohols, typically coniferyl alcohol units or a combination of coniferyl and syringyl alcohols.

Mammals do not produce the enzymes necessary to hydrolyze the $\beta$-1-4-glucosidic bonds of cellulose. Such enzymes, however, are produced by a number of microorganisms, and such microorganisms are found, e.g., in a symbiotic relationship in the stomachs of ruminants to facilitate the digestion of lignocellulosic materials.

Microbial or enzymatic degradation of lignocellulose is often relatively ineffective and/or unacceptably slow for many agricultural and commercial purposes. It has been found that the degree of crystallinity of the lignocellulose material and the presence of lignin and hemicellulose are significant factors in impeding the degradation or decomposition of lignocellulose. Indeed, the crystalline regions of cellulose and regions of lignocellulosic materials containing a substantial amount of lignin are notoriously resistant to biological degradation.

For these reasons, the abundant lignocellulosic agricultural residues, including straw, chaff, corn stover, and the like, are waste products that presently have little or no commercial value. Moreover, these materials decompose slowly in the environment and often present waste disposal problems.

Various prior art processes have been developed to reduce the crystallinity of lignocellulosic materials and/or to remove lignin from these materials. One of the most effective is an alkaline hydrogen peroxide pretreatment that disrupts the crystallinity of the cellulose and solubilizes the lignin. See, e.g., J. Gould, Alkaline Peroxide Delignification of Agricultural Residues to Enhance Enzymatic Saccharification, Biotechnology and Bioengineering 26:46–52 (1984); Wei et al., Effect of Hydrogen Peroxide Pretreatment on the Structural Features and the Enzymatic Hydrolysis of Rice Straw, Biotechnology and Bioengineering, 27:1418–1426 (1985); and J. Gould, U.S. Pat. No. 4,649,113. By treating lignocellulosic materials (particularly those from non-woody plants) with dilute hydrogen peroxide at a pH of about 11.5, lignocellulosic materials may be converted into material that is easily digested by ruminant animals. See M. Kerley, et al., Alkaline Hydrogen Peroxide Treatment Unlocks Energy and Agricultural By-Products, Science 230: 820–822 (1985). In this study, lambs fed on alkaline hydrogen peroxide-treated wheat straw gained weight at a rate comparable to that of lambs consuming a diet composed predominantly of corn.

Although humans lack the ability to digest cellulose, cellulose is nevertheless desirable in human nutrition as a source of dietary fiber. It has been demonstrated that cellulose fiber from straw or other sources that has been processed with alkaline hydrogen peroxide can be milled into a white powder and used as a replacement for up to 40% of the flour in baked goods, without any perceptible deleterious effect on the resulting product. Indeed, bread products made with wheat flour and 30% cellulose fiber form a gluten network having a higher tensile strength than that of bread made with flour alone. The fiber-containing bread also exhibits an increased volume.

Use of such lignocellulose fibers as dietary fiber can simultaneously increase the non-nutritive dietary fiber content and decrease the caloric value of the products made with the fiber. In light of public health concerns related to inadequate consumption of dietary fiber and excess consumption of calories, both of these factors are believed to be highly desirable.

One of the major costs involved in the alkaline hydrogen peroxide process for treatment of lignocellulosic materials is the cost of the hydrogen peroxide. Moreover, a significant concern related to the use of that process is the disposal of the solubilized hemicellulose and lignin in the effluent stream of the process. Both of these factors could have a significant impact on the economics and feasibility of commercializing this lignocellulose treatment process.

SUMMARY OF THE INVENTION

The present invention provides a process for treating lignocellulosic materials to render them digestible by ruminants and also to provide a source of dietary fiber for humans, and includes a method for generating hydrogen peroxide on site from low cost feedstocks. The hydrogen peroxide is generated in the form of a dilute stream and is appropriate for use in treatment of lignocellulosic agricultural residues.

In one embodiment of the process, the dilute hydrogen peroxide stream generated also includes formaldehyde as a co-product, which is converted to formate ion. This formate ion is useful in treatment of silage materials to inhibit microbial degradation of protein. Thus, the hydrogen peroxide and formate ion together can greatly enhance and preserve the nutritional value of many livestock feed materials. Thus, in accordance with one aspect of the present invention, there is provided a method for treating lignocellulosic material, comprising the steps of enzymatically converting a lower alkyl alcohol to hydrogen peroxide and an aldehyde, and then treating lignocellulosic material with an aqueous reaction mixture, comprising the hydrogen peroxide produced by the enzymatic conversion step, to remove lignin therefrom. In a preferred embodiment, the enzymatic conversion step produces aqueous hydrogen peroxide at a concentration between about 0.1% and 10%, v/v, more preferably between 0.5% or 0.75% and 5%, v/v, and the aqueous reaction mixture comprises 0.1% to 10% hydrogen peroxide, v/v, more preferably between 0.5% or 0.75% and 5%, v/v. Alternatively, more concentrated hydrogen peroxide concentrations may be used, e.g., as much as 20% or 40%, w/v.

In accordance with a further embodiment of the invention, the process includes the step of separating the aldehyde from the hydrogen peroxide prior to the treating step.

In some embodiments of the invention, the enzymatic conversion step provides an effluent comprising the hydrogen peroxide and the effluent is directed into a reaction zone to form the reaction mixture.

In other embodiments of the invention, the treating step comprises reacting hydrogen peroxide, formaldehyde, and hydroxy ion to form formate ion, and then reacting the alkaline hydrogen peroxide/formate mixture with the lignocellulosic material. In a preferred embodiment, about half of the hydrogen peroxide in the effluent is consumed to quantitatively convert formaldehyde to formate ion, and the remainder of the $H_2O_2$ is used to delignify the lignocellulosic material.

In any of the processes of the invention, the process may also include the step of generating alcohol oxidase enzyme by culturing alcohol-oxidase-producing microorganisms on a carbon source, where the alcohol oxidase enzyme produced by those microorganisms is used in the enzymatic conversion step. This process also includes the removal of catalase enzyme activity produced by many such microorganisms. Catalase activity converts hydrogen peroxide to water. The removal of catalase enzymes, in one embodiment, is accomplished by utilizing non-catalase producing (cat$^-$) mutants of the microorganisms.

In still another preferred embodiment of the invention, the enzymatic conversion step comprises introducing water, lower alkyl alcohol, and an alcohol oxidase into a reaction zone to form a reaction solution, maintaining the temperature the reaction solution below about 10° C., and enzymatically converting the alcohol in the reaction solution into an aldehyde and hydrogen peroxide.

In yet another embodiment of the present invention, the effluent generated in the enzymatic conversion step comprises dilute hydrogen peroxide and formaldehyde, and the process further comprises converting the formaldehyde to formic acid prior to the treating step.

The invention also includes a method for delignifying lignocellulosic materials, comprising the steps of obtaining a delignification mixture comprising at least 5% $H_2O_2$, w/w, preferably 15% to 20% $H_2O_2$, w/w, and from 0.1M to 5.0M, preferably 1.2M to 4.8M, available OH$^-$, then combining the delignification mixture with a lignocellulosic substrate to delignify it to the desired degree.

In accordance with still another aspect of the present invention, there is provided an apparatus for treating lignocellulosic materials, comprising an enzymatic conversion zone adapted to enzymatically convert alcohol to aldehyde and hydrogen peroxide; a delignification zone; means for transferring an effluent comprising aqueous hydrogen peroxide from the conversion zone to the delignification zone; means for adding sized lignocellulosic material to the delignification zone; and means for separating solid delignified material in the delignification zone from a liquid. In preferred embodiments, the apparatus may further comprise a liquid reaction mixture in the enzymatic conversion zone comprising alcohol oxidase enzyme, alcohol, and water, and may include sized lignocellulosic material and basic, aqueous hydrogen peroxide in the delignification zone, wherein the hydrogen peroxide has been produced in the conversion zone. Additionally, the apparatus may further include formate ion in the delignification zone, wherein the formate ion is from formaldehyde produced in the conversion zone.

In accordance with yet another aspect of the present invention, the apparatus also includes a fermenter adapted to grow alcohol oxidase-producing yeast and means for transferring alcohol oxidase from the fermenter into the conversion zone. It further may include means for separating enzyme from the effluent and returning it to the conversion zone, a sizer for chopping or sizing lignocellulosic material, and means interposed between the conversion zone and the delignification zone for removing aldehyde from the effluent. The aldehyde removing means may advantageously comprise a distillation apparatus, a separation column, or other suitable apparatus.

In accordance with a further embodiment, the invention includes an apparatus for treating lignocellulosic material, comprising an enzymatic conversion zone containing a liquid reaction mixture comprising alcohol oxidase enzyme, alcohol, and water; a delignification zone containing lignocellulosic material in basic aqueous hydrogen peroxide; and means for transferring effluent from the enzymatic conversion zone to the delignification zone. It may further comprise a fermenter containing a fermentation mixture of a carbon source and an alcohol oxidase-producing organism.

DETAILED DESCRIPTION OF THE INVENTION

Figure 1:
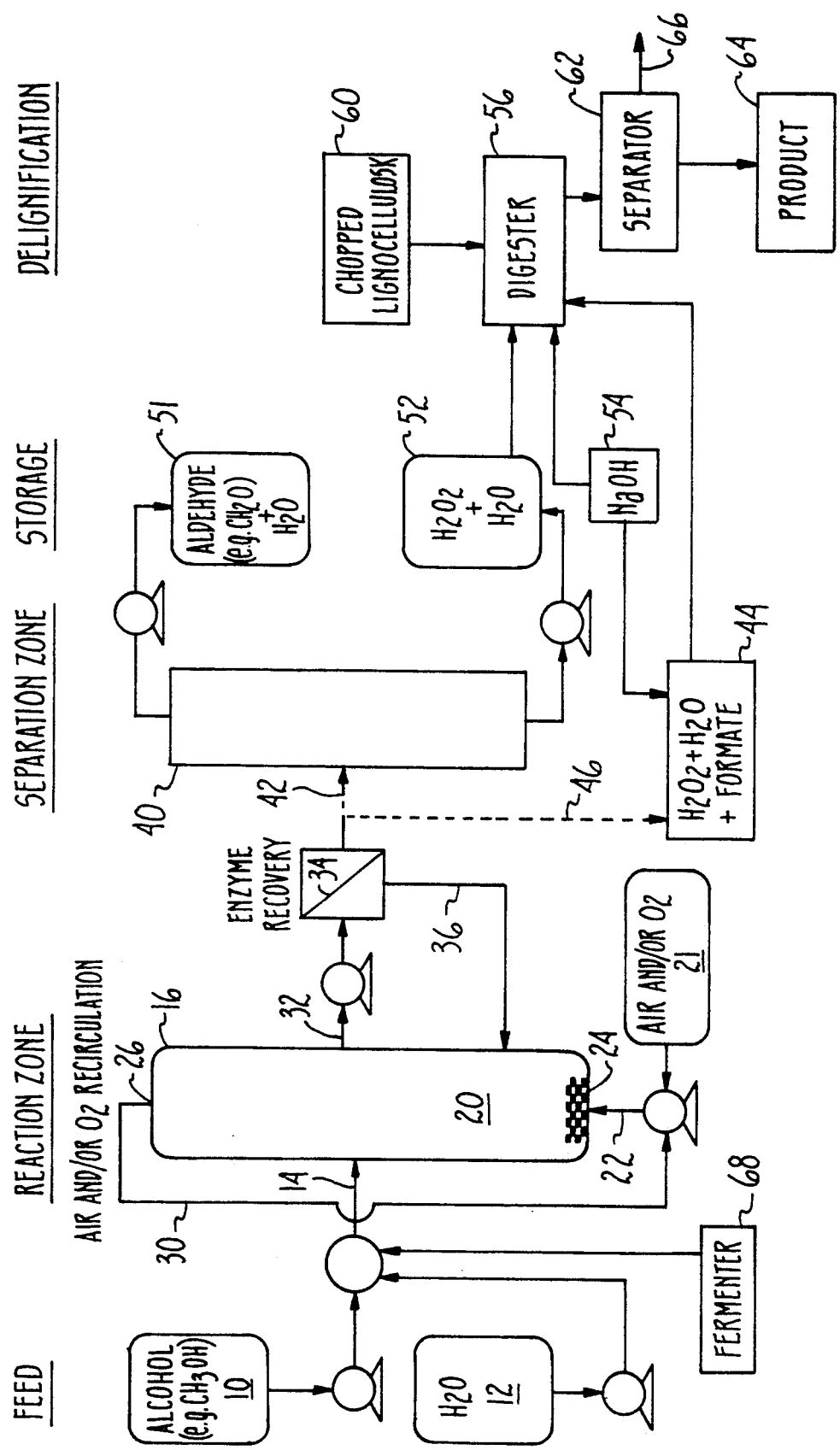
FIG. 1 is a schematic representation of an apparatus for use in practicing the delignification process of the present invention.

The first aspect of the process of the present invention involves generating an oxidizing moiety to react with the lignocellulosic material. This oxidizing moiety is preferably hydrogen peroxide (or, more particularly, the oxygen or hydroxyl radical formed therefrom).

The present invention utilizes an alcohol oxidase enzyme acting on an inexpensive alcohol substrate, such as methanol, to produce hydrogen peroxide and an aldehyde, such as formaldehyde. Suitable processes are disclosed, for example, in two co-pending U.S. applications, Ser. No. 825,856, filed Feb. 4, 1986, and Ser. No. 047,658, filed May 8, 1987, the disclosures of which are hereby incorporated by this reference.

In its general form, the process for generating the hydrogen peroxide from an alcohol, such as methanol, begins with the step of providing an aqueous reaction mixture, comprising alcohol and alcohol oxidase enzyme. The preferred alcohol is methanol; however, other alcohols having from 1 to 5 carbon atoms, such as ethanol or propanol, may also be utilized.

Yeasts in the genera Pichia, Candida, Torulopsis, and Hansenula possess a methanol utilizing pathway which involves the fixation of formaldehyde (derived from methanol) to xylulose-5-phosphate, the conversion of that product into dihydroxyacetone and glyceraldehyde-3-phosphate, and the eventual regeneration of xylulose-5-phosphate. It appears that all alcohol oxidase enzymes from organisms that use this pathway may be used in the present invention. The steps of the reaction are carried out in the subcellular peroxisomes. The first step of that pathway involves the oxidation of methanol to formaldehyde and hydrogen peroxide and is catalyzed by alcohol oxidase. (The literature refers to this enzyme both as alcohol oxidase and methanol oxidase. As used herein, these terms are considered to be synonymous.)

The alcohol oxidase used in the present invention may advantageously be that produced by the organism Hansenula polymorpha, and particularly the alcohol oxidase produced by the Hansenula polymorpha strain designated by the American Type Culture Collection (ATCC), 13021 Parklawn Drive, Rockville, Md., U.S.A., by its accession No. 34438. This Hansenula polymorpha strain is commercially available from ATCC.

We have found that Hansenula polymorpha ATCC 34438 is surprisingly resistant to high substrate and product concentrations. Indeed, at room temperature, this particular alcohol oxidase maintains its activity in concentrations of alcohol as high as about 5%, and in similar concentrations of formaldehyde and hydrogen peroxide.

Other preferred alcohol oxidases are those that are functionally identical to the alcohol oxidase derived from Hansenula polymorpha ATCC 34438, or to the alcohol oxidase from Pichia pastoris. The base sequence of the alcohol oxidase gene for Hansenula polymorpha ATCC 34438 and the amino acid sequence for the subunits making up this enzyme have been identified for this strain. See Ledeboer et al. (1985) Nuc. Acids Res. 9, 3063-3082, which is hereby incorporated by reference. Other alcohol oxidases that may be used include those from Hansenula polymorpha DL-1 ATCC 26012, Candida boidinii, and Torulopsis. Appropriate screening procedures for enzyme activity, catalytic capacity and product tolerance will be apparent from the disclosures that follow, and should be used to select alcohol oxidase enzymes having optimal properties.

In order to be optimally usable in the process of the present invention, it is desired that the product stream produced by action of the alcohol oxidase on its substrate have a concentration of at least 0.5% hydrogen peroxide, more preferably at least 0.75% or 1.0% hydrogen peroxide. Accordingly, if one desires to avoid the necessity of an expensive concentration step, these hydrogen peroxide concentration requirements in the product stream define the minimum performance criteria for enzymes suitable for use in the process of the present invention.

In other words, the alcohol oxidase enzyme selected for use in the present process preferably can tolerate alcohol concentrations of 0.5%, and more preferably 1% or 2%, and can tolerate hydrogen peroxide concentrations of at least 0.5%, more preferably 0.75% or 1%, under standard enzyme assay conditions.

In addition to the naturally-occurring enzymes produced by the foregoing organisms, the process of the present invention may also utilize enzymes produced by recombinant DNA technology, and/or by chemical modification of enzyme obtained from living organisms. Thus, for example, it is contemplated that the alcohol oxidase gene from Hansenula polymorpha ATCC 34438 may be cloned and expressed in any suitable host, and the resulting enzyme may be utilized in the process of the present invention. Similarly, other enzymes having an active site the same as or substantially equivalent to that of Hansenula polymorpha ATCC 34438, or otherwise functionally equivalent, may be utilized.

It has further been unexpectedly discovered that certain unconventional process temperatures greatly facilitate the enzymatic capacity and the substrate end product toleration of the alcohol oxidase used in the present invention. For example, the alcohol oxidase of Hansenula polymorpha ATCC 34438 exhibits as much as a 20 fold increase in substrate concentration required to inactivate the enzyme or decrease the enzymatic capacity thereof. Other alcohol oxidase enzymes, such as alcohol oxidase from Pichia, exhibit similar optimization of properties at temperatures below room temperature and, indeed, below 0° C.

The process temperature for formation of the hydrogen peroxide containing the stream may vary, depending on the particular alcohol oxidase used. For any particular enzyme and desired product and substrate concentration, the optimal temperature may be readily determined by empirical methods. However, we have determined that optimum process efficiencies are realized at about $-22°$ C. with the alcohol oxidase of Hansenula polymorpha ATCC 34438, utilizing a methanol substrate concentration of about 40%-50%. When operating at subfreezing temperatures, the substrate functions as an antifreeze maintaining the reaction mixture of water, alcohol, and alcohol oxidase (together with any product formed) in a liquid state.

The process can be used at temperatures maintained below 10° C., preferably below about 5° C. or 0° C., more preferably below about $-5°$ C., and most preferably below about $-15°$ C. or $-20°$ C. The process can be used at temperatures down to a lower limit of about $-40°$ C. or $-50°$ C., depending on the freezing point of the alcohol-water mixture. It can be used over a broad pH range from 6.0 to 9.0, preferably at pH 6.0 to 7.0 for temperatures below 10° C.

Although higher production efficiencies and substrate product concentrations may be obtained through modification of the temperature of the reaction mixture, in many applications it will be desirable to perform the enzymatic reaction at room temperature. This will minimize capital costs by limiting the necessity of providing refrigeration equipment for reducing the temperature of the reaction mixture. Although low temperatures may optimize the enzymatic capacity and the product concentration of the effluent stream from the reaction zone, it is important to recognize that high hydrogen peroxide concentrations are not required for the process of the present invention. Indeed, a 1% or 2% hydrogen peroxide concentration in the effluent stream from the reaction zone is usually sufficient. It should be recognized, however, that the elimination of refrigeration equipment will result in somewhat less efficient utilization of the enzyme, thereby increasing enzyme requirements.

The enzymatic conversion of methanol to hydrogen peroxide and formaldehyde is an aerobic process. Indeed, the rate limiting step is often the rate at which oxygen can be solubilized in the reaction mixture to be utilized by the enzyme in the conversion process. Accordingly, to provide rapid and efficient reaction, the reaction mixture may be maintained under hyperbaric conditions, and oxygen may be delivered to the mixture by sparging air or an oxygen-enriched gas mixture, or even pure oxygen, through the reaction mixture or through liquids feeding into the reaction mixture.

Reaction conditions are optimum at $O_2$ concentrations of about 0.8 mM. At air saturation, a liquid under ambient atmospheric pressure will have an oxygen concentration of about 0.2 mM. Since oxygen dissolves in liquid in proportion to its pressure in the gas phase, its concentration in liquid may be increased by enriching the oxygen content in the reaction atmosphere, or by increasing the pressure over the reaction mixture, or both, to increase oxygen content at least four-fold. The oxygen-containing gas may be bubbled through or perfused into the reaction mixture and it may also be recirculated.

The alcohol oxidase enzyme can be used in the highly purified state, or in the form of a soluble cell-free extract or a crude whole cell preparation from Hansenula polymorpha or other microorganism. Since alcohol oxidase can be induced to very high levels in the organism, and there are no purification losses, crude whole cell preparations are advantageous. However, the cells also contain catalase, an enzyme which catalyzes the dissociation of hydrogen peroxide to water and oxygen, and hydrogen peroxide production is inversely proportion to catalase activity. One means to reduce catalase activity takes advantage of the rapid decay of catalase. Crude alcohol oxidase stored at 4° C. for several days will be substantially depleted of active catalase enzyme. Barratti, et al. Biotechnology and Bioengineering 20, 333-338 (1978). Depletion may be monitored by means of an assay for catalase activity. Moreover, catalase function appears to be inhibited under the reaction conditions of the presently-disclosed process.

Alternatively, catalase activity can be substantially eliminated by increasing the pH of a crude cell extract or other catalase-containing composition to at least about 8.5 or 9.0 for a period of time sufficient to inactivate the catalase. At pH 8.5 or 9.0, the time required for catalase inactivation is about 6-10 hours. At pH 10 or above, catalase inactivation occurs within about 1-2 hours. The alcohol oxidase enzyme, in contrast to catalase, is resistant to inactivation at high pH.

Catalase activity may be virtually eliminated by using alcohol oxidase preparations derived from catalse-minus (cat$^-$) mutant yeast strains. Such cat yeast strains are described in European Patent Application of Unilever PLC, Publication Number 0 242 007 (A1).

Insoluble crude cell preparations are advantageous because they conveniently segregate the enzyme from its reaction products. "Activated" cells, having increased efficiency of interaction between substrate and enzyme, can be produced by partially disrupting the cell membrane through such methods as mechanical shearing, freeze-thaw, osmotic rupture, or a detergent treatment to produce a "leaky" cell membrane. The strong cationic agent cetyl trimethyl ammonium bromide (CTAB) is an appropriate detergent. Thus, for example, cells may be treated for about 5 minutes in a solution of 0.02% to 0.2% CTAB, and washed several times in potassium phosphate buffer before used for the enzyme reaction. Alternatively, leaky mutant yeast cells may be utilized. Such leaky mutants can be developed, e.g., in accordance with the method of B. Zurbiggen, et al., J. Biotech. 4:159-170 (1986).

Alcohol oxidase enzyme may also be used as a soluble cell-free extract. The use of soluble cell free extracts avoids purification losses and provides an enzyme preparation that can be uniformly dispersed in the reaction mixture. Highly purified enzyme may be prepared according to conventional enzyme purification procedures in order to produce catalase-free alcohol oxidase of high specific activity. Purified enzyme is used to determine specific activity or other enzyme parameters as part of the process of screening for suitable cell strains.

A. Preparation of Enzyme

The alcohol oxidase enzyme may be produced by transcription and translation of an appropriate gene, such as a Hansenula polymorpha gene that has been cloned and amplified by genetic engineering techniques. However, the preferred technique is simply the growth of Hansenula polymorpha and the induction of alcohol oxidase synthesis in that organism.

1. Growth of Hansenula polymorpha and Enzyme Induction

Growth media for yeast are well known in the art. Hansenula polymorpha and other similar organisms may be grown in a glucose, xylose, or methanol medium. A suitable glucose medium may contain, by weight, 0.4% $NH_4Cl$, 0.1% $KH_2PO_4$, 0.1% $K_2HPO_4$, 0.05% $MgSO_4.7H_2O$, 0.05% yeast extract, and 1% glucose. A suitable xylose medium would substitute xylose for glucose in concentrations of from 0.5% to 3%. A suitable methanol medium would contain the same nitrogen, potassium, phosphate, and sulfate sources, together with from 0.3% to 3% by volume methanol.

The growth rates of the yeast on glucose and on xylose are comparable. The cell doubling time in glucose is somewhat less than 2.5 hours. Similarly, on xylose, the cells double in about 2.5 hours. This is significantly faster than the doubling time on methanol, which is closer to 4 hours. When the yeast is grown in a glucose or xylose medium, alcohol oxidase production is induced by diluting the yeast 1:10 from the glucose medium into a 1-3% by volume methanol medium and growing to late log phase, approximately 24 hours at 28° C.

Growing the yeast on xylose is advantageous because growth rates of the yeast on xylose are faster in comparison to growth on methanol and, when cat$^-$ mutants are grown, less selection pressure for strains to mutate back to catalase-plus (cat$^+$).

Alternatively, yeast may be grown in a methanol-limited chemostat in accordance with the method of Van Dijken, et al, Arch. Microbiol. 111, 137-144 (1976).

In the presence of methanol, the resulting Hansenula polymorpha contains at least 20% of the protein of a cell-free extract in the form of alcohol oxidase.

Alcohol oxidase may also be prepared by genetic engineering techniques by cloning the gene coding for that enzyme into a multicopy plasmid in a desired host microorganism.

2. Enzyme Purification

In the first step of a suitable enzyme purification procedure, the cells are disrupted and homogenized. A phosphate buffer may be used to adjust the pH prior to homogenization to about 7.5. After cell disruption, cell debris can be removed by centrifugation. The supernatant solution represents a cell-free enzyme extract.

A particularly preferred purification technique utilizes an ion exchange column to purify alcohol oxidase from the crude cell-free extract. This purification procedure is a relatively fast, inexpensive, and efficient method for producing large quantities of protein in a short period of time. The protein that elutes from a DEAE-cellulose column, for example, is free of cellular catalase. The alcohol oxidase from Hansenula polymorpha elutes from the DEAE-cellulose, using a salt-gradient elution, at approximately 0.3M NaCl. At this stage the enzyme is approximately 80–90% pure. It is also possible to shorten this procedure further by eluting alcohol oxidase from the column using a batchwise elution rather than a salt gradient. The enzyme will be of a lower purity, but since the only contaminant that substantially affects the reaction is catalase (which catalyzes the reaction $2H_2O_2 \rightarrow 2H_2O + O_2$) and since catalase does not bind to the DEAE-cellulose under the conditions used, the extraneous contamination will be of little consequence. Residual catalase may be determined by appropriate assay. See, e.g., Luck, H., Methods of Enzymatic Analysis 885–894 (H. Bergemeyer ed. 1963).

One example of an effective ion-exchange purification technique is set forth in Example 1, below.

B. Enzyme Properties

To screen for alcohol oxidase activity suitable for use in the process of the present invention, the purified enzyme (purified at least to be free of catalase activity) is assayed for its activity in the presence of high concentrations of methanol, i.e., 1%, 2%, 5%, 7% and 10% by volume. It is also assayed for its activity in the presence of high concentrations of products, hydrogen peroxide and formaldehyde.

1. Assays

Alcohol oxidase assay: Alcohol oxidase activity is determined by the conversion of methanol to hydrogen peroxide and formaldehyde ($\mu$moles product/min/mg protein). A solution containing from $1 \times 10^{-4}$ to $1 \times 10^{-3}$ units/ml alcohol oxidase, 0.2M methanol, and 0.1M potassium phosphate buffer (pH 7.5) is incubated for 30 minutes at 37° C. The reaction is stopped with the addition of 1/15 volume 4M HCl, bringing the total volume to 1 ml. The products $H_2O_2$ and/or $CH_2O$ are then assayed and specific activity is calculated as $\mu$moles/min/mg protein.

Hydrogen peroxide assay: Hydrogen peroxide is assayed using peroxidase. The 1 ml reaction mixture contains: 2.5 $\mu$g peroxidase, 1 mM ABTS (2,2'-azino-di-[3-ethyl-benzthioazoline sulphate-6]), and 100 mM potassium phosphate buffer pH 7.5. The reaction mixtures are incubated at 37° C. for 10 min. Reactions are stopped by the addition of 67 $\mu$l of 4M HCl and are read at 410 nm. Concentrations of hydrogen peroxide are determined by comparison to a standard curve (1 $O.D._{410} = 18.5$ nmoles $H_2O_2$/ml).

Formaldehyde assay: Formaldehyde is assayed using Nash reagent (2M Ammonium acetate, 50 mM acetic acid, 20 mM acetylacetone). The formaldehyde solution is mixed with an equal amount of Nash reagent and incubated at 37° C. for 30 min. At the end of the incubation period the reactions are stopped by adding 1/15th volume (67 $\mu$l/ml) 4M HCl and are read at 412 nm. Concentrations of formaldehyde are determined by comparison to a standard curve (1 $O.D._{412} = 248$ nmoles $CH_2O$/ml).

C. Process Conditions for Oxidation of Lower Alkyl Alcohols

The enzyme retains activity over a pH range of from 6.5 to 9.0 under standard assay conditions at 37° C. The preferred process pH at reduced temperature is from 6.0 to 7.0, and a pH of 6.5 is particularly preferred. In certain processes, it may be desirable to use a relatively volatile buffer, such as $NH_4HCO_3$, which can be removed from product by distillation in the purification step.

The preferred buffers are phosphate and carbonate or bicarbonate buffers, including potassium phosphate, sodium bicarbonate, and ammonium bicarbonate, all adjusted to about pH 6.5.

Although the preferred alcohol oxidase enzyme exhibits its highest affinity for methanol, it also has a significant degree of activity on other lower alkyl and lower alkaline alcohols. Straight chain alcohols of four or fewer carbon atoms are particularly preferred. Aside from methanol, the enzyme exhibits greatest activity with ethanol and allyl alcohol, converting them, respectively, to acetaldehyde and acrolein.

Alcohol oxidase has a low affinity for its substrates, (Km methanol, 2.0 mM; Km oxygen, 0.4 mM), and the rate of product formation has been shown to increase significantly when either methanol or oxygen or both are in excess (see: Van Dijken, et al., Arch. Microbiol., 111, 137 (1976)). Because methanol is infinitely soluble in water, its excess is easily achieved. The concentration of oxygen at air saturation (0.2 mM), however, is rate limiting. Under conditions of excess methanol, 0.8 mM to 1.0 mM oxygen is required for the enzyme to approach maximum velocity. Correlation between enzyme velocity and enzyme concentration is therefore improved by increasing the partial pressure of oxygen in the reaction environment. Under the combination of low temperature and increased methanol concentration, the solubility of oxygen in the mixture is improved.

D. Enzyme Performance Under Conditions of Low Temperature and High Substrate Concentration The preferred alcohol oxidase from Hansenula polymorpha ATCC 34438 exhibits increased catalytic capacity (g product/g enzyme) under conditions of decreased temperature and increased methanol concentration. At low enzyme concentration (0.055 $\mu$g/ml) and air saturation of oxygen where product accumulation is less than 0.003%, catalytic capacity of the enzyme at $-15°$ C. and 30% methanol is greatly increased over that at 37° C. and 40 mM methanol. A sixty-fold increase in catalytic capacity was accomplished with a fifteen-fold decrease in reaction velocity. Conditions of low temperature and increased methanol concentration similarly extend the catalytic capacity of commercially available yeast alcohol oxidase from Pichia pastoris in a parallel manner. Pichia pastoris alcohol oxidase is obtained from Provesta Corporation, Bartlesville, Okla.

Once the hydrogen peroxide-containing effluent stream from the enzymatic reaction process is obtained, it may be used as is, or may be subjected to purification steps, separation steps, or chemical conversion steps prior to use in the delignification portion of the process of the present invention.

In accordance with one aspect of the process of the present invention, the product stream from the enzymatic process (which preferably contains about 1.0% hydrogen peroxide) may be adjusted to a pH between about 11 and 12, preferably about 11.5 or 11.6, and then used directly to treat straw or other lignocellulosic material. The pH adjustment may advantageously be effected through the use of sodium hydroxide, NaOH, or other bases. Where the product stream of the enzymatic conversion process is to be thus utilized directly, it is preferred that the initial concentration be about 2% hydrogen peroxide (by volume). That is because mixtures of hydrogen peroxide and formaldehyde undergo what is known as the Fenton reaction. (Fenton, Proc. Chem. Soc. 9:113 (1893).) Under basic (and more slowly under acidic) conditions, formaldehyde reacts with hydrogen peroxide and water to form formic acid. (More specifically, in the presence of base, formate ion is formed.) The stoichiometry of this reaction is 2 moles of formaldehyde to 1 mole of hydrogen peroxide. Because the enzymatic process forms hydrogen peroxide and formaldehyde from methanol in equimolar quantities, this reaction will consume approximately 50% of the hydrogen peroxide in converting the formaldehyde to formate. The reaction is quantitative; thus, 100% of the formaldehyde is converted to formate.

In a minor modification of the foregoing process, the base (such as sodium hydroxide) may be added to the product stream sufficiently prior to use of that stream to treat lignocellulosic materials so as to permit complete conversion of formaldehyde to formic acid prior to such treatment of lignocellulosic materials. Still another variation of the process includes removing the formate from the stream prior to treating the lignocellulosic material. This may be done, e.g., through the use of an anionic ion exchange material, such as that sold by the Dow Chemical Company under the trade designation DOWEX.

Use of a product stream containing formate is particularly advantageous in the treatment of animal feedstocks, including silage materials. Formic acid is presently used in silage treatment to prevent conversion of protein in the silage to nonprotein nitrogen compounds. Thus, treatment of silage with the product stream of the present invention, where formate is included in the treatment mixture, will both increase the digestibility of the carbohydrate present in the silage and decrease the amount of undesired microbial decomposition of protein present in the raw silage material.

In another embodiment of the present invention, separation steps are performed on the product stream from the enzymatic reaction prior to using the hydrogen peroxide from that stream to treat lignocellulosic material. These separation steps may separate the hydrogen peroxide in the product stream from the unreacted alcohol or from the formaldehyde or both. Suitable separation steps may include distillation steps and membrane processes. Removal of all the formaldehyde prior to treatment of lignocellulosic materials is particularly desirable when the end product of the process is food fiber intended for human consumption.

E. Separation of Reaction Products

The products in the effluent of the enzymatic conversion process may be separated from each other by distillation. The boiling point of formaldehyde in aqueous solution (formal) is 96° C. at atmospheric pressure and that of hydrogen peroxide is 152° C. at atmospheric pressure. Any methanol that may still be unreacted and therefore still remains in the product mixture would distill off with formaldehyde. Further separation of the methanol and formaldehyde is ordinarily not required since methanol is commonly added to formaldehyde solutions as a stabilizer. Therefore, the purification step preferably involves distilling off formaldehyde and methanol and water at approximately 100° C. The remaining hydrogen peroxide can be further concentrated by distilling off the remaining water as required.

In addition to distillation techniques, separation of aldehydes from hydrogen peroxide may be accomplished by using prevaporation membranes or other membrane processes such as those described by Strathman, Trends in Biotechnology, 3, 112, (No. 5, 1985). Super-critical fluid extraction systems such as those manufactured by Milton Roy Company, 201 Ivyland Road, Ivyland, Pa. 18974-0577 also may be used to separate reaction products.

The lignocellulosic material used in the process of the present invention may be virtually any lignocellulosic material, particularly non-woody lignocellulosic materials. Such materials include grass, straw from virtually all cereal crops, chaff, bran, corn stover, and any of the other abundant agricultural waste products that presently have little or no commercial value.

The conversion process itself comprises reacting the lignocellulosic material with hydrogen peroxide at a concentration of between 0.1% and 10%, preferably between about 0.75% and 5%, and at a pH between about 10.5 and 12.5, preferably between about 11 and 12. The lignocellulosic material is preferably chopped into small pieces prior to the conversion process, and is typically added to the reaction mixture in an amount of about 15 to about 500 g/l, more preferably about 20–50 g/l. It is also preferred that the hydrogen peroxide be present in concentrations sufficient to fully react with the lignocellulosic material. The process conditions disclosed in U.S. Pat. No. 4,649,113 to Gould are particularly appropriate, and that disclosure is incorporated herein by this reference.

Finely divided lignocellulosic material is mixed with the hydrogen peroxide containing material at ambient temperature. The amount of time required to solubilize the lignin and hemicellulose present in the treated material varies depending on the particular material being treated and the average size of the chopped material. For example, wheat straw treated with 1% hydrogen peroxide at a pH of about 11.5 is substantially delignified in 4 to 6 hours at about 25° C. Maximal delignification of virtually all materials suitable for use in the present process may be accomplished in 24 hours or less.

After incubation of the lignocellulosic material with the alkaline hydrogen peroxide mixture for a period of time sufficient to effect the desired solubilization of lignin and hemicellulose, the solids in the reaction mixture are separate from the liquid phase. The solids are generally in the form of a nearly white particulate material. The filtrate liquid contains lignin and hemicellulose.

F. Process Apparatus

A suitable apparatus for the continuous-type conversion of alcohol into hydrogen peroxide and treatment of lignocellulosic materials in accordance with the present invention is shown schematically in FIG. 1. (In a continuous conversion process, substrate is continuously added and product is continuously removed.) An alcohol source 10 and a water source 12 are provided. An inlet line 14 introduces alcohol and water into a reaction zone 16. In FIG. 1, the reaction zone 16 is preferably a refrigerated, pressured chamber or container or a plurality of chambers or containers. Alternatively, an ambient temperature chamber may be used. The reaction zone may alternatively comprise an elongated structure. One example of such a structure is a tube. The reaction zone 16 contains a reaction mixture 20. This reaction mixture contains water, alcohol that is introduced into the reaction zone through inlet line 14, alcohol oxidase enzyme, and oxygen. Due to the action of the alcohol oxidase enzyme on the alcohol, the reaction mixture 20 also contains aldehyde and hydrogen peroxide.

Means such as gas inlet 22 are provided for introducing an oxygen-containing gas from an oxygen source 21 into the reaction zone 16. This gas is preferably oxygen gas, $O_2$. The reaction zone 16 is ordinarily pressurized to increase the rate and degree of oxygen dissolving into the reaction mixture 20. The preferred oxygenation technique is a sparging technique. The reaction zone 16 may advantageously include porous material 24 or other conventional materials for dispersing the oxygen as bubbles throughout the reaction zone 16. Gas is removed from the reaction zone 16 through the gas outlet 26. Means 30 for recirculating gas from the gas outlet 26 back to the gas inlet 22 may also be provided. Such a recirculating means 30 has the advantage of both conserving oxygen and reintroducing any vaporized aldehyde back into the reaction zone 16 and the reaction mixture 20. Recirculation also prevents expelling formaldehyde into the environment. Inside the reaction zone 16 or connected to the reaction zone 16 is preferably a means for agitating or mixing the reaction mixture 20. In FIG. 1, the agitation means is the porous material 24 and the oxygen-containing gas passing through the porous material 24 to form bubbles that continuously agitate and mix the reaction mixture 20 in the reaction zone 16.

The reaction zone 16 is bounded at its outlet 32 by an enzyme recovery means 34. The enzyme recovery means 34 may be a dialysis membrane or an ultrafiltration material. The enzyme recovery means 34 is capable of passing species of small molecular weight, such as aldehydes and hydrogen peroxide, while retaining high molecular weight species, particularly the alcohol oxidase enzyme used in the present invention, which has a molecular weight of 560,400. In order to prevent a flow-restricting accumulation of enzyme on the enzyme recovery means 34, the flow rate per unit area of the enzyme recovery means 34 is kept low. For any given throughput, this is done by making the semipermeable membrane very large or by utilization of a tangential flow membrane apparatus. Periodically, the enzyme recovery means may be washed to remove accumulated enzyme. This can be done by introducing a backflow of liquid through the enzyme recovery means 34 or by directing a liquid flow across, rather than through, the enzyme recovery means 34. Enzyme recovered from the enzyme recovery means 34 is recycled back into the reaction zone 16 and through a line 36.

From the reaction zone 16, the aldehyde and hydrogen peroxide produced in the reaction zone pass through the outlet 32 and the enzyme recovery means 34 into a separation zone 40, as indicated by arrow 42 in the embodiment of the invention that involves such separation. The separation zone 40 may comprise a distillation apparatus for separating aldehyde from hydrogen peroxide. Alternatively, the aldehyde and hydrogen peroxide produced in the reaction zone 16 may go from the enzyme recovery means 34 into a formate formation vessel 44 as indicated by arrow 46.

In practice, the volatile aldehydes can be separated from the hydrogen peroxide as a gaseous mixture in the separation zone. In the case of formaldehyde, this gaseous mixture also contains water and small quantities of methanol. In the case of formaldehyde no further purification will ordinarily be necessary, despite the presence of methanol and water in the end product in vessel 51, because formaldehyde is ordinarily sold as an aqueous solution and that aqueous solution is usually stabilized with small quantities of methanol.

In the separation step, the hydrogen peroxide is removed from the separation zone as an aqueous solution to storage vessel 52.

In the embodiment of the invention in which the formaldehyde is not removed from the effluent of the reaction zone 16, the aldehyde, such as formaldehyde, may be converted into the complementary acid ion, such as formate ion, in the formate formation vessel 44, by addition of a base, such as sodium hydroxide from a sodium hydroxide tank 54. The formate (or other ion) formation may be carried out in a separate formate formation vessel 44, as illustrated in FIG. 1; alternatively, the product stream from the reaction zone 16 may go directly into a digester 56, and addition of sodium hydroxide or other base in the digester will also result in formate (or other ion) formation.

The delignification process of the present invention occurs in the digester 56. In this process, appropriately sized lignocellulosic material from a sizer 60 is introduced into the digester 56, and an aqueous solution of the hydrogen peroxide and water, and optionally, formate ion or other carboxylic acid ion, is introduced into the digester 56, either from the hydrogen peroxide storage vessel 52, directly from the enzymatic reaction zone 16, or from the formate formation vessel 44. The sizer may chop or otherwise size the lignocellulosic material by any appropriate technique. It is preferred that the lignocellulosic material be sized to chopped pieces of between 2 cm and more finely comminuted material, such as 10 mesh to 100 mesh.

Sodium hydroxide or other base is added to the digester 56 to arrive at a pH in the digester between about 10.5 and 12.5, more preferably, between about 11 and 12. Optimum process pH appears to be about 11 or 12, depending on the desired product. For animal feed, a pH of 11 results in less mass loss. On the other hand, a process pH of 12 is more desirable for making food fiber for human consumption, because more hemicellulose is removed at this pH. During the digestion process, the pH may change; accordingly, additional acid or base may be added during the digestion process to maintain the pH at the desired level. Any unreacted formaldehyde will be converted in the digester 56 into formate ion by reaction with hydroxy ion and hydrogen peroxide. Initial hydrogen peroxide concentration in the digester 56 is preferably about 1% to 2%.

Delignification proceeds in the digester 56 until the desired level of delignification is achieved. This may be anywhere from about 1 hour to over 24 hours, depending on the material and the concentration of the reactants, and the intended end use of the material.

Once the delignification process is complete, the mixture from the digester 56 is processed through a separator 62, to separate the solids from the liquid. The solids comprise the desired delignified cellulosic material, and may be dried and stored in a product storage area 64.

Separation may be effected in any conventional manner, such as by filtration, siphoning, or centrifugation.

A batch-type process according to the present invention may also be practiced with the apparatus of FIG. 1. Water, alcohol, and enzyme are introduced into the reaction zone 16 through inlet line 14 to form a reaction mixture 20 and to fill up the reaction zone 16 to the desired level. The reaction mixture 20 remains in the reaction zone 16, with an oxygenating gas being introduced into the reaction zone 16 through a gas inlet 22 and porous material 24. The gas is removed from gas outlet 26 and recirculated through recirculation means 30. The bubbling of the oxygen-containing gas through the reaction mixture 20 provides agitation and mixing so that the reaction mixture 20 is substantially homogenous. When the reaction has gone to the desired stage of completion, reaction mixture 20 is removed from the reaction zone 16 through the outlet 32. The enzyme is removed from the reaction mixture 20 by the enzyme recovery means 34, and the reaction mixture proceeds into the separation zone 40 or the formate formation vessel 44. The reaction zone 16 may then be refilled with reaction mixture 20, and the process repeated. The remainder of the process proceeds as above.

In one example of a batch process using 50% methanol in water (w/v), 1.9 mg/ml crude Hansenula polymorpha ATCC 34438 extract, under 80 psi pure oxygen, the reaction mixture after 3.6 days at $-22°$ C. contained 6.5% formaldehyde and 5.1% hydrogen peroxide. Extrapolated endpoint values for product are 7.7% formaldehyde and 6.9% hydrogen peroxide.

The present invention also includes a modified process for rapidly delignifying lignocellulosic materials with concentrated reagents. We have discovered that, contrary to the techniques for alkaline $H_2O_2$ delignification disclosed in the literature, surprisingly complete and/or rapid delignification of relatively dry lignocellulosic substrates can be achieved in accordance with our process. The pH of the conversion process using these concentrated reagents does not fall within the narrow range required in the process of Gould, U.S. Pat. No. 4,649,113, and the delignification can be substantially more complete than that achieved by the Gould process.

In accordance with our concentrated reagent process, we combine dry lignocellulosic material, preferably from nonwoody plants, with an aqueous solution of base and $H_2O_2$, the latter being present in a concentration of at least 5%, preferably at least 10%, and more preferably at least 15%, 20%, or 25%, w/w. The molar concentration of the base may vary widely, without dramatically affecting the delignification. As a general rule, sufficient base is added to provide a concentration of available $OH^-$ ion of about 0.1M to about 8M, preferably about 0.5M to about 5M. $OH^-$ ion is considered "available" within the meaning of the present application if it is dissociated or it will dissociate from its cation during the progress of the reaction in question. Strong bases, such as NaOH, are preferred as the source of $OH^-$ ion. The upper limit of the concentration of $H_2O_2$ and base in the mixture is determined only by practical considerations of the concentration of available reagents and the dilution of one reagent upon combination with the other. The $H_2O_2$ used in the process is preferably prepared by enzymatic conversion of alcohol, as previously described, followed by concentration steps.

It is preferred that the reaction mixture be applied to dry or damp lignocellulosic substrate to provide a weight ratio of $H_2O_2$ to substrate of from about 0.1:1 to about 10:1, more preferably from about 0.5:1 to about 2:1. The reaction is rapid, with the major portion of the delignification occurring within 5 minutes, although residual delignification proceeds for up to 24 hours, depending on the substrate and the ratio of $H_2O_2$ to substrate.

It is contemplated that our process for treating dry materials with concentrated reagents will be particularly useful in the agricultural industry, and the present invention includes in situ treatment of lignocellulosic materials. Thus, for example, the reagents could be applied to bales of straw, bulk silage, and the like in the field or in the storage facility. After the reaction has gone to completion, an acid may be added or the material may be washed to bring it to a pH suitable for the intended use of the delignified material. The delignification reagents could be applied to the substrate by spraying, dipping, mixing, or by any other suitable method.

The following detailed Examples will serve to illustrate the processes of the present invention; however, it is not intended that they shall in any way limit the scope of the invention beyond what is set forth in the claims appended hereto.

Example 1: Enzyme Purification

Hansenula polymorpha cells are collected by centrifugation (5,000×g, 10 min.) and resuspended in 50 mM potassium phosphate buffer, pH 7.5 (using a ratio of cells:buffer of approximately 1:2). Cells are disrupted in a "Beadbeater" homogenizer for 3 min. total (6 bursts of 30 sec. with 5 min. cooling intervals on ice). The enzyme solution is then applied to a DEAE-cellulose column (Whatman) which has been equilibrated with 50 mM potassium phosphate buffer, pH 7.5. The column is washed with 50 mM potassium buffer, pH 7.5, until all unabsorbed proteins are washed from the column. Alcohol oxidase is eluted from the DEAE-cellulose with a linear salt gradient from 0–0.6M NaCl in 50 mM potassium phosphate buffer pH 7.5. Fractions containing alcohol oxidase are pooled and concentrated by vacuum dialysis. Purification data are set forth in Table 1.

TABLE 1

| | Purification of Alcohol Oxidase From Hansenula Polymorpha | | | | |
|---|---|---|---|---|---|
| Step | Volume (ml) | Protein (mg/ml) | Total Protein (mg) | Activity ($\mu$mol/min/ml) | Total Activity ($\mu$mol/min) | Specific Activity ($\mu$mol/$H_2O_2$/min/mg) |
| Extract | 67 | 2.1 | 141 | 8.6 | 578 | 4.1 |
| DEAE cellulose | 130 | 0.26 | 34 | 43 | 553 | 16.5 |
| Vacuum | 8.0 | 3.5 | 28 | 58.3 | 466 | 16.6 |

The purity of the enzyme produced in Example 1 is determined by SDS-polyacrylamide gel electrophoresis. The alcohol oxidase remaining after the final concentration step has a purity greater than 95%. The activity of the enzyme is expressed in standard units of μmols product/min/mg protein, at 37° C.

Example 2: Continuous Ambient Temperature Conversion of Methanol to Formaldehyde and Hydrogen Peroxide In a continuous process for the conversion of methanol to formaldehyde and hydrogen peroxide, 10 l 4% by volume aqueous methanol solution is added to a reaction vessel. The solution is buffered to pH 7.5 with a potassium phosphate buffer (0.1 molar). 1.0 g methanol oxidase enzyme from Example 1 is added, providing an enzyme concentration of 100 μg/ml in the reaction vessel. The reaction vessel is pressurized with oxygen to 10 atmospheres, and 4 mmoles/min. oxygen is sparged through the mixture. The gas is removed from the top of the reaction vessel. The gas is then recirculated through the reaction vessel. Air or oxygen is added to the recirculated gas in order to maintain excess oxygen in solution. An ultrafiltration material having a molecular weight cut-off of 100,000 is provided at the inlet and at the outlet of the reaction vessel. Buffered aqueous methanol solution containing 4% methanol by volume is continuously introduced into the reaction zone at the rate of 2.5 ml/min. The reaction products are continuously removed from the reaction vessel through the ultrafiltration material. The ultrafiltration material at the outlet of the reaction vessel is periodically back-flushed to remove enzyme accumulating thereon. That enzyme is then recirculated into the reaction vessel. Fresh enzyme is added to the reaction vessel at the rate of 0.5 g/day to maintain the active enzyme concentration at approximately 100 μg/ml. The reaction mixture removed from the vessel contains approximately 4% formaldehyde, 4% hydrogen peroxide, and a small percentage of methanol.

Example 3: Continuous Conversion of Methanol to Formaldehyde and Hydrogen Peroxide at Reduced Temperature In a continuous process for the conversion of methanol to formaldehyde and hydrogen peroxide, 10 l 40% by volume aqueous methanol solution is added to a reaction vessel. The solution is adjusted to pH 7.0 and the temperature of the system is reduced to about −22° C. and maintained continuously at that temperature. A quantity of alcohol oxidase enzyme is added to provide an enzyme concentration of about 0.2 mg/ml in the reaction vessel. To oxygenate the reaction solution, 4 mmoles/min oxygen can be sparged through the mixture. Alternatively, the reaction vessel is pressurized with air to about 5 atmospheres, and the pressurized air is sparged through the mixture. The gas is removed from the top of the reaction vessel. Air or oxygen is added to the recirculated gas in order to maintain excess oxygen in solution.

An ultrafiltration material having a molecular weight cut-off of about 100,000 is provided at the inlet and at the outlet of the reaction vessel. Methanol and water are continuously introduced into the reaction zone of the reactive mixture to maintain the methanol concentration at about 40%. The reaction products are continuously removed from the reaction vessel through the ultrafiltration material. The ultrafiltration material at the outlet of the reaction vessel is periodically back-flushed or otherwise treated to remove materials accumulating thereon. Enzyme from the ultrafilter is recirculated into the reaction vessel. Fresh enzyme is added to the reaction vessel to maintain the active enzyme concentration at approximately 0.2 mg/ml. The reaction mixture removed from the vessel contains approximately 0.2–0.4% formaldehyde, 0.2–0.4% hydrogen peroxide, and about 40% methanol, by volume, with an average yield of 7 grams formaldehyde plus 8 grams hydrogen peroxide per 1,000 units enzyme.

Example 4: Batchwise Conversion of Methanol to Formaldehyde and Hydrogen Peroxide at Reduced Temperature A reaction vessel was charged with an aqueous reaction mixture of 50% methanol, 60 units/ml Hansenula polymorpha ATCC 34438 alcohol oxidase, and 0.3M potassium phosphate buffer (pH 7.4). The mixture was maintained under an oxygen atmosphere at 80 psi at −18° C. for 12 hours. Oxygen transport into the reaction mixture was by diffusion. The mixture was then analyzed, and was found to contain 6.1% $H_2O_2$ and 4.8% $CH_2O$.

Example 5: Alkaline Hydrogen Peroxide Treatment of Lignocellulosic Material With and Without Formate To study the effect of formate ion in the delignification process of the present invention, comparative tests were performed.

Wheat straw (1.5 g, chopped into pieces of approximately 1 cm) was combined with an aqueous solution of 0.75% $H_2O_2$, the pH of which was adjusted to 11.6 with NaOH. The weight ratio of straw to $H_2O_2$ in the solution was 4:1. The mixture was maintained at rom temperature for 24 hours, after which the mixture was filtered and the solids were washed 2× in water and dried.

The above procedure was repeated in identical fashion, except that the delignification mixture also contained 0.45M NaCOOH, sodium formate.

The relative extent of delignification was measured by the digestibility of the treated material with cellulase enzyme (Trichoderma viride). Ten mg of treated material was combined with 20 Sigma units cellulase in 1 ml 0.5M citrate buffer, pH 4.8. The cellulase was permitted to digest the delignified material overnight at 50° C., and then the solution was assayed for glucose content in accordance with the standard procedure set forth by G. L. Miller, Anal. Chem. 31:426–428 (1959), using dinitrosalicylic acid and glucose standards. The percentage digestion was determined by the weight ratio of glucose (after the cellulase digestion) to the delignified starting material (before the digestion) ×100%.

The $H_2O_2$-treated straw exhibited a degree of digestion of 53%, while the $H_2O_2$/formate treated straw exhibited 64% digestion, demonstrating the salutary effect of formate on the alkaline $H_2O_2$ delignification process of the present invention.

Example 6: Delignification of Other Agricultural Waste Materials with Dilute Alkaline Hydrogen Peroxide Samples of rice straw and cane bagasse were treated with aqueous, alkaline 1% hydrogen peroxide, pH 11.6 at a ratio of substrate to $H_2O_2$ of 2:1, following the general procedures of Example 5. The cellulase digestibility of untreated substrate to the treated material was determined as in the previous Example. The glucose assay revealed that treatment in accordance with this example increased the cellulase digestibility of rice straw from 11.4% to 47.1%, and of cane bagasse from 0.0% to 61.5%. This is particularly significant in the case of cane bagasse, which appears to be converted from a nutritionally useless material to a material having significant food value for ruminants.

Example 7: In Situ Delignification of Wheat Straw

Three reaction mixtures were prepared, each containing one gram dry wheat straw, chopped to approximately 0.2 mm, was combined with 3 ml 33% $H_2O_2$ (a 1:1 straw/$H_2O_2$ ratio. w/w). To one of the mixtures there was also added 0.5 ml 12M NaOH, to another one 1.0 ml 12M NaOH, and to the remaining one, 2.0 ml 12M NaOH. Thus, the first mixtures contained 28% $H_2O_2$, the second 25% $H_2O_2$, and the third 20% $H_2O_2$. These mixtures were permitted to react at room temperature, and portions of the straw were removed at 5 minutes, 30 minutes, 2 hours, and 24 hours. These portions were washed 2× in water to stop the reaction, vacuum filtered, and air dried. Percentage digestibility was then measured with cellulase enzyme as set forth in Example 5, and the data were averaged. The results are set forth in Table 2:

TABLE 2

Cellulase Digestibility of Wheat Straw After In Situ Delignification with Concentrated Reagents

| | 5 min | 30 min | 2 hr | 24 hr |
|---|---|---|---|---|
| 28% $H_2O_2$/1.7M NaOH | 50% | 63% | 75% | 87% |
| 25% $H_2O_2$/3.0M NaOH | 69% | 78% | 89% | 91% |
| 20% $H_2O_2$/4.8M NaOH | 65% | 80% | 81% | 96% |
| Control (untreated straw) | | | approx. | 16% |

These data demonstrate that significant increases in digestibility can be achieved by using concentrated reagents, even when treating dry lignocellulosic substrate, as compared to treatment with dilute reagents. Substantial delignification occurs in a very short period of time.

What is claimed is:

1. An apparatus for treating lignocellulosic materials, comprising:
   a source for alcohol and a source for water;
   an enzymatic conversion means for enzymatically converting said alcohol to aldehyde and hydrogen peroxide including means for maintaining the temperature of said enzymatic conversion reaction means at less than 0° C.;
   a delignification means for delignifying said lignocellulosic material, a source of basic material for adjusting the pH;
   means for transferring an effluent comprising aqueous hydrogen peroxide from said conversion means to said delignification means;
   means for adding sized lignocellulosic material to said delignification means; and
   means for separating solid delignified material in said delignification means from a liquid therein.

2. The apparatus of claim 1, further comprising:
   a liquid reaction mixture in said enzymatic conversion means comprising alcohol oxidase enzyme, alcohol, and water.

3. The apparatus of claim 1 or 2, further comprising:
   chopped lignocellulosic material basic material and, aqueous hydrogen peroxide in said delignification means, wherein said hydrogen peroxide has been produced in said conversion means.

4. The apparatus of claim 1, further comprising formate ion in said delignification means, wherein said formate ion is from formaldehyde produced in said conversion means.

5. The apparatus of claim 1, further comprising:
   a fermenter adapted to grow alcohol oxidase-producing yeast; and
   means for transferring alcohol oxidase from said fermenter into said conversion means.

6. The apparatus of claim 1, further comprising:
   means for separating enzyme from said effluent and returning it to said conversion means.

7. The apparatus of claim 1, further comprising a chopper for chopping said lignocellulosic material.

8. The apparatus of claim 1, further comprising means interposed between said conversion zone and said delignification means for removing aldehyde from said effluent.

9. The apparatus of claim 8, wherein said aldehyde removing means comprises a distillation apparatus.

10. An apparatus for treating lignocellulosic material, comprising:
    an enzymatic conversion means containing a liquid reaction mixture comprising alcohol oxidase enzyme, alcohol, and water, said means for maintaining the reaction mixture at a temperature of less than 0° C.;
    a delignification means containing lignocellulosic material in basic aqueous hydrogen peroxide; and
    means for transferring effluent from said enzymatic conversion means to said delignification means.

11. The apparatus of claim 10, further comprising:
    a fermenter containing a fermentation mixture of a carbon source and an alcohol oxidase-producing organism.

* * * * *